United States Patent
Foley et al.

(10) Patent No.: US 8,436,185 B2
(45) Date of Patent: May 7, 2013

(54) PHARMACEUTICALLY ACCEPTABLE SALTS OF 2-{4-[(3S)-PIPERIDIN-3-YL]PHENYL}-2H-INDAZOLE-7-CARBOXAMIDE

(75) Inventors: Jennifer R. Foley, Garwood, NJ (US); Robert Darrin Wilson, Hoddesdon Herts (GB)

(73) Assignee: Merck Sharp & Dohme Corp., Rahway, NJ (US)

( * ) Notice: Subject to any disclaimer, the term of this patent is extended or adjusted under 35 U.S.C. 154(b) by 106 days.

(21) Appl. No.: 12/811,922

(22) PCT Filed: Jan. 8, 2009

(86) PCT No.: PCT/GB2009/000041
§ 371 (c)(1),
(2), (4) Date: Jul. 7, 2010

(87) PCT Pub. No.: WO2009/087381
PCT Pub. Date: Jul. 16, 2009

(65) Prior Publication Data
US 2010/0286203 A1    Nov. 11, 2010

Related U.S. Application Data

(60) Provisional application No. 61/010,333, filed on Jan. 8, 2008.

(51) Int. Cl.
*C07D 211/32*    (2006.01)
*A61K 31/445*    (2006.01)

(52) U.S. Cl.
USPC .......................................... 546/199; 514/322

(58) Field of Classification Search .................. 546/199; 514/322
See application file for complete search history.

(56) References Cited

U.S. PATENT DOCUMENTS

| | | | |
|---|---|---|---|
| 6,100,283 A | 8/2000 | Griffin et al. | |
| 6,310,082 B1 | 10/2001 | Griffin et al. | |
| 6,448,271 B1 | 9/2002 | Lubisch et al. | |
| 6,509,365 B1 | 1/2003 | Lubisch et al. | |
| 6,696,437 B1 | 2/2004 | Lubisch et al. | |
| 6,737,421 B1 | 5/2004 | Lubish et al. | |
| 7,041,675 B2 | 5/2006 | Lubisch et al. | |
| 7,087,637 B2 | 8/2006 | Grandel et al. | |
| 8,071,623 B2 * | 12/2011 | Jones et al. | 514/322 |
| 2006/0063926 A1 | 3/2006 | Ma et al. | |
| 2006/0229289 A1 | 10/2006 | Zhu et al. | |
| 2006/0229351 A1 | 10/2006 | Zhu et al. | |
| 2007/0112047 A1 | 5/2007 | Penning et al. | |
| 2007/0259937 A1 | 11/2007 | Giranda et al. | |

FOREIGN PATENT DOCUMENTS

| | | |
|---|---|---|
| CA | 2349227 | 10/1999 |
| EP | 0879820 | 12/2001 |
| WO | WO97/04771 | 2/1997 |
| WO | WO99/59973 | 11/1999 |
| WO | WO00/26193 | 5/2000 |
| WO | WO00/29384 | 5/2000 |
| WO | WO00/32579 | 6/2000 |
| WO | WO00/64878 | 11/2000 |
| WO | WO00/68206 | 11/2000 |
| WO | WO01/21615 | 3/2001 |
| WO | WO01/57038 | 8/2001 |
| WO | WO01/85687 | 11/2001 |
| WO | WO02/068407 | 9/2002 |
| WO | WO03/007959 | 1/2003 |
| WO | WO03/062234 | 7/2003 |
| WO | WO03/106430 | 12/2003 |
| WO | WO2004/014861 | 2/2004 |
| WO | WO2005/066136 | 7/2005 |
| WO | WO2007/041357 | 4/2007 |
| WO | WO2007113596 | 10/2007 |
| WO | WO2008084261 | 7/2008 |

OTHER PUBLICATIONS

Bastin et al Organic Process Research and Development 2000, 4, 427-435.*

Thomas, et al., Molecular Cancer Research, vol. 6 (3), pp. 945-956 (2007), "Preclinical selection of a novel poly (ADP-ribose) polymerase inhibitor for clinical trial".

* cited by examiner

*Primary Examiner* — John Mabry
(74) *Attorney, Agent, or Firm* — Yong Zhao; David A. Muthard; Matthew A. Leff

(57) ABSTRACT

The present invention relates to pharmaceutically acceptable salts of an amide substituted indazole which are inhibitors of the enzyme poly(ADP-ribose)polymerase (PARP), previously known as poly(ADP-ribose)synthase and poly(ADP-ribosyl) transferase. The compounds of the present invention are useful as mono-therapies in tumors with specific defects in DNA-repair pathways and as enhancers of certain DNA-damaging agents such as anticancer agents and radiotherapy. Further, the compounds of the present invention are useful for reducing cell necrosis (in stroke and myocardial infarction), down regulating inflammation and tissue injury, treating retroviral infections and protecting against the toxicity of chemotherapy.

1 Claim, No Drawings

PHARMACEUTICALLY ACCEPTABLE SALTS OF 2-{4-[(3S)-PIPERIDIN-3-YL]PHENYL}-2H-INDAZOLE-7-CARBOXAMIDE

PRIORITY CLAIM

This application is a §371 National Stage Application of PCT/GB2009/000041, filed on Jan. 8, 2009 which claims priority from U.S. Provisional Application Ser. No. 61/010,333, filed on Jan. 8, 2008.

BACKGROUND OF THE INVENTION

The present invention relates to pharmaceutically acceptable salts of an amide substituted indazole which are inhibitors of the enzyme poly(ADP-ribose)polymerase (PARP), previously known as poly(ADP-ribose)synthase and poly (ADP-ribosyl)transferase. The compounds of the present invention are useful as mono-therapies in tumors with specific defects in DNA-repair pathways and as enhancers of certain DNA-damaging agents such as anticancer agents and radiotherapy. Further, the compounds of the present invention are useful for reducing cell necrosis (in stroke and myocardial infarction), down regulating inflammation and tissue injury, treating retroviral infections and protecting against the toxicity of chemotherapy.

Poly(ADP-ribose) polymerase (PARP) constitute a super family of eighteen proteins containing PARP catalytic domains (*Bioessays* (2004) 26:1148). These proteins include PARP-1, PARP-2, PARP-3, tankyrase-1, tankyrase-2, vault-PARP and TiPARP. PARP-1, the founding member, consists of three main domains: an amino (N)-terminal DNA-binding domain (DBD) containing two zinc fingers, the automodification domain, and a carboxy (C)-terminal catalytic domain.

PARP are nuclear and cytoplasmic enzymes that cleave $NAD^+$ to nicotinamide and ADP-ribose to form long and branched ADP-ribose polymers on target proteins, including topoisomerases, histones and PARP itself (*Biochem. Biophys. Res. Commun.* (1998) 245:1-10).

Poly(ADP-ribosyl)ation has been implicated in several biological processes, including DNA repair, gene transcription, cell cycle progression, cell death, chromatin functions and genomic stability.

The catalytic activity of PARP-1 and PARP-2 has been shown to be promptly stimulated by DNA strand breakages (see *Pharmacological Research* (2005) 52:25-33). In response to DNA damage, PARP-1 binds to single and double DNA nicks. Under normal physiological conditions there is minimal PARP activity, however, upon DNA damage an immediate activation of PARP activity of up to 500-fold occurs. Both PARP-1 and PARP-2 detect DNA strand interruptions acting as nick sensors, providing rapid signals to halt transcription and recruiting the enzymes required for DNA repair at the site of damage. Since radiotherapy and many chemotherapeutic approaches to cancer therapy act by inducing DNA damage, PARP inhibitors are useful as chemo- and radiosensitizers for cancer treatment. PARP inhibitors have been reported to be effective in radio sensitizing hypoxic tumor cells (U.S. Pat. No. 5,032,617, U.S. Pat. No. 5,215,738 and U.S. Pat. No. 5,041,653).

Most of the biological effects of PARP relate to this poly (ADP-ribosyl)ation process which influences the properties and function of the target proteins; to the PAR oligomers that, when cleaved from poly(ADP-ribosyl)ated proteins, confer distinct cellular effects; the physical association of PARP with nuclear proteins to form functional complexes; and the lowering of the cellular level of its substrate $NAD^+$ (*Nature Review* (2005) 4:421-440).

Besides being involved in DNA repair, PARP may also act as a mediator of cell death. Its excessive activation in pathological conditions such as ischemia and reperfusion injury can result in substantial depletion of the intercellular $NAD^+$, which can lead to the impairment of several $NAD^+$ dependent metabolic pathways and result in cell death (see *Pharmacological Research* (2005) 52:44-59). As a result of PARP activation, $NAD^+$ levels significantly decline. Extensive PARP activation leads to severe depletion of $NAD^+$ in cells suffering from massive DNA damage. The short half-life of poly(ADP-ribose) results in a rapid turnover rate, as once poly(ADP-ribose) is formed, it is quickly degraded by the constitutively active poly(ADP-ribose) glycohydrolase (PARG). PARP and PARG form a cycle that converts a large amount of $NAD^+$ to ADP-ribose, causing a drop of $NAD^+$ and ATP to less than 20% of the normal level. Such a scenario is especially detrimental during ischemia when deprivation of oxygen has already drastically compromised cellular energy output. Subsequent free radical production during reperfusion is assumed to be a major cause of tissue damage. Part of the ATP drop, which is typical in many organs during ischemia and reperfusion, could be linked to $NAD^+$ depletion due to poly(ADP-ribose) turnover. Thus, PARP inhibition is expected to preserve the cellular energy level thereby potentiating the survival of ischemic tissues after insult. Compounds which are inhibitors of PARP are therefore useful for treating conditions which result from PARP mediated cell death, including neurological conditions such as stroke, trauma and Parkinson's disease.

PARP inhibitors have been demonstrated as being useful for the specific killing of BRCA-1 and BRCA-2 deficient tumors (*Nature* (2005) 434:913-916 and 917-921; and *Cancer Biology & Therapy* (2005) 4:934-936).

PARP inhibitors have been shown to enhance the efficacy of anticancer drugs (*Pharmacological Research* (2005) 52:25-33), including platinum compounds such as cisplatin and carboplatin (*Cancer Chemother Pharmacol* (1993) 33:157-162 and *Mol Cancer Ther* (2003) 2:371-382). PARP inhibitors have been shown to increase the antitumor activity of topoisomerase I inhibitors such as Irinotecan and Topotecan (*Mol Cancer Ther* (2003) 2:371-382; and *Clin Cancer Res* (2000) 6:2860-2867) and this has been demonstrated in in vivo models (*J Natl Cancer Inst* (2004) 96:56-67).

PARP inhibitors have been shown to restore susceptibility to the cytotoxic and antiproliferative effects of temozolomide (TMZ) (see *Curr Med Chem* (2002) 9:1285-1301 and *Med Chem Rev Online* (2004) 1:144-150). This has been demonstrated in a number of in vitro models (*Br J Cancer* (1995) 72:849-856; *Br J Cancer* (1996) 74:1030-1036; *Mol Pharmacol* (1997) 52:249-258; *Leukemia* (1999) 13:901-909; *Glia* (2002) 40:44-54; and *Clin Cancer Res* (2000) 6:2860-2867 and (2004) 10:881-889) and in vivo models (*Blood* (2002) 99:2241-2244; *Clin Cancer Res* (2003) 9:5370-5379 and *J Natl Cancer Inst* (2004) 96:56-67). PAPR inhibitors have also been shown to prevent the appearance of necrosis induced by selective N3-adenine methylating agents such as $MeOSO_2(CH_2)$-lexitropsin (Me-Lex) (*Pharmacological Research* (2005) 52:25-33).

PARP inhibitors have been shown to act as radiation sensitizers. PARP inhibitors have been reported to be effective in radiosensitizing (hypoxic) tumor cells and effective in preventing tumor cells from recovering from potentially lethal (*Br. J. Cancer* (1984) 49 (Suppl. VI):34-42; and *Int. J. Radiat. Bioi.* (1999) 75:91-100) and sub-lethal (*Clin. Oncol.* (2004)

16(1):29-39) damage of DNA after radiation therapy, presumably by their ability to prevent DNA strand break rejoining and by affecting several DNA damage signaling pathways.

PARP inhibitors have also been shown to be useful for treating acute and chronic myocardial diseases (see *Pharmacological Research* (2005) 52:34-43). For instance, it has been demonstrated that single injections of PARP inhibitors have reduced the infarct size caused by ischemia and reperfusion of the heart or skeletal muscle in rabbits. In these studies, a single injection of 3-amino-benzamide (10 mg/kg), either one minute before occlusion or one minute before reperfusion, caused similar reductions in infarct size in the heart (32-42%) while 1,5-dihydroxyisoquinoline (1 mg/kg), another PARP inhibitor, reduced infarct size by a comparable degree (38-48%). These results make it reasonable to assume that PARP inhibitors could salvage previously ischemic heart or reperfusion injury of skeletal muscle tissue (*PNAS* (1997) 94:679-683). Similar findings have also been reported in pigs (*Eur. J. Pharmacol.* (1998) 359:143-150 and *Ann. Thorac. Surg.* (2002) 73:575-581) and in dogs (*Shock.* (2004) 21:426-32).

PARP inhibitors have been demonstrated as being useful for treating certain vascular diseases, septic shock, ischemic injury and neurotoxicity (*Biochim. Biophys. Acta* (1989) 1014:1-7; *J. Clin. Invest*. (1997) 100: 723-735). Oxygen radical DNA damage that leads to strand breaks in DNA, which are subsequently recognized by PARP, is a major contributing factor to such disease states as shown by PARP inhibitor studies (*J. Neurosci. Res.* (1994) 39:38-46 and *PNAS* (1996) 93:4688-4692). PARP has also been demonstrated to play a role in the pathogenesis of hemorrhagic shock (*PNAS* (2000) 97:10203-10208).

PARP inhibitors have been demonstrated as being useful for treatment of inflammation diseases (see *Pharmacological Research* (2005) 52:72-82 and 83-92).

It has also been demonstrated that efficient retroviral infection of mammalian cells is blocked by the inhibition of PARP activity. Such inhibition of recombinant retroviral vector infections has been shown to occur in various different cell types (*J. Virology*, (1996) 70(6):3992-4000). Inhibitors of PARP have thus been developed for use in anti-viral therapies and in cancer treatment (WO 91/18591).

In vitro and in vivo experiments have demonstrated that PARP inhibitors can be used for the treatment or prevention of autoimmune diseases such as Type I diabetes and diabetic complications (*Pharmacological Research* (2005) 52:60-71).

PARP inhibition has been speculated as delaying the onset of aging characteristics in human fibroblasts (*Biochem. Biophys. Res. Comm.* (1994) 201(2):665-672 and *Pharmacological Research* (2005) 52:93-99). This may be related to the role that PARP plays in controlling telomere function (*Nature Gen.*, (1999) 23 (476-80).

The vast majority of PARP inhibitors to date interact with the nicotinamide binding domain of the enzyme and behave as competitive inhibitors with respect to $NAD^+$ (*Expert Opin. Ther. Patents* (2004) 14:1531-1551). Structural analogues of nicotinamide, such as benzamide and derivatives were among the first compounds to be investigated as PARP inhibitors. However, these molecules have a weak inhibitory activity and possess other effects unrelated to PARP inhibition. Thus, there is a need to provide potent inhibitors of the PARP enzyme.

Structurally related PARP inhibitors have previously been described. WO 1999/59973 discloses amide substituted benzene rings fused to 5 membered heteroaromatic rings; WO2001/85687 discloses amide substituted indoles; WO 1997/04771, WO 2000/26192, WO 2000/32579, WO 2000/64878, WO 2000/68206, WO 2001/21615, WO 2002/068407, WO 2003/106430 and WO 2004/096793 disclose amide substituted benzoimidazoles; WO 2000/29384 discloses amide substituted benzoimidazoles and indoles; and EP 0879820 discloses amide substituted benzoxazoles. Structurally related indazolecarboxamides are also disclosed in WO2007/113596 and WO07/113,596.

It has now surprisingly been discovered that amide substituted indazoles of the present invention exhibit particularly high levels of inhibition of the activity of poly(ADP-ribose) polymerase (PARP). Thus the compounds of the present invention are particularly useful as inhibitors of PARP-1 and/or PARP-2. They also show particularly good levels of cellular activity, demonstrating good anti-proliferative effects in BRCA1 and BRCA2 deficient cell lines.

The present invention provides pharmaceutically acceptable salts of the compound of formula I:

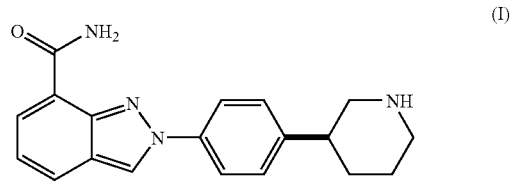

(I)

2-{4-[(3S)-Piperidin-3-yl]phenyl}-2H-indazole-7-carboxamide

Particular compounds of the present invention are:
(3S)-3-{4-[7-(Aminocarbonyl)-2H-indazol-2-yl]phenyl}piperidinium 4-methylbenzenesulfonate;
(3S)-3-{4-[7-(Aminocarbonyl)-2H-indazol-2-yl]phenyl}piperidinium sulfate;
(3S)-3-{4-[7-(Aminocarbonyl)-2H-indazol-2-yl]phenyl}piperidinium benzenesulfate;
(3S)-3-{4-[7-(Aminocarbonyl)-2H-indazol-2-yl]phenyl}piperidinium fumarate;
(3S)-3-{4-[7-(Aminocarbonyl)-2H-indazol-2-yl]phenyl}piperidinium succinate;
and stereoisomers and tautomers thereof.

A particular compound of the present invention is:
(3S)-3-{4-[7-(aminocarbonyl)-2H-indazol-2-yl]phenyl}piperidinium 4-methylbenzenesulfonate;
or a stereoisomer or tautomer thereof.

A particular compound of the present invention is:
(3S)-3-{4-[7-(Aminocarbonyl)-2H-indazol-2-yl]phenyl}piperidinium sulfate;
or a stereoisomer or tautomer thereof.

A particular compound of the present invention is:
(3S)-3-{4-[7-(Aminocarbonyl)-2H-indazol-2-yl]phenyl}piperidinium benzenesulfate;
or a stereoisomer or tautomer thereof.

A particular compound of the present invention is:
(3S)-3-{4-[7-(Aminocarbonyl)-2H-indazol-2-yl]phenyl}piperidinium fumarate;
or a stereoisomer or tautomer thereof A particular compound of the present invention is:
(3S)-3-{4-[7-(Aminocarbonyl)-2H-indazol-2-yl]phenyl}piperidinium succinate;
or a stereoisomer or tautomer thereof.

The present invention also includes within its scope N-oxides of the compounds. In general, such N-oxides may be formed on any available nitrogen atom. The N-oxides may be formed by conventional means, such as reacting the compounds with oxone in the presence of wet alumina.

The present invention includes within its scope prodrugs of the compounds. In general, such prodrugs will be functional derivatives of the compounds which are readily convertible in vivo into the required compounds. Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds, for example, hydrates.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

The compounds may exist in different isomeric forms, all of which are encompassed by the present invention.

The compounds may exist in a number of different polymorphic forms.

The free base of the compounds of the present invention can be protonated at the N atom(s) of an amine and/or N containing heterocycle moiety to form a salt. The term "free base" refers to the amine compounds in non-salt form. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts can be synthesized from the compounds of formula I which contain basic moieties by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents.

Thus, pharmaceutically acceptable salts of the instant invention can be prepared from compounds of formula I by reacting with an inorganic, organic acid or polymeric acid. For example, conventional non-toxic salts include those derived from acids such as toluenesulfonic acid, sulfuric acid, benzenesulfonic acid, fumaric acid or succinic acid, especially toluenesulfonic acid.

Preferably, a pharmaceutically acceptable salt of this invention contains 1 equivalent of a compound of formula (I) and 1, 2 or 3 equivalent of an acid. In an embodiment a pharmaceutically acceptable salt of this invention contains 2 equivalent of a compound of formula (I) and 1 equivalent of an acid.

The term toluenesulfonic acid can be used interchangeably with 4-methylbenzene sulfonic acid, and toluene sulfonates can also be referred to as tosylate salts.

The preparation of the pharmaceutically acceptable salts described above and other typical pharmaceutically acceptable salts is more fully described by Berg et al (1977) *J. Pharm. Sci., 'Pharmaceutical Salts'*, 66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of the invention can be used in a method of treatment of the human or animal body by therapy.

The invention provides compounds for use in the treatment or prevention of conditions which can be ameliorated by the inhibition of poly(ADP-ribose)polymerase (PARP) (see, for example, *Nature Review Drug Discovery* (2005) 4:421-440).

Thus, the present invention provides a pharmaceutically acceptable salt of a compound of formula I for use in the manufacture of a medicament for the treatment or prevention of conditions which can be ameliorated by the inhibition of poly(ADP-ribose)polymerase (PARP).

The present invention also provides a method for the treatment or prevention of conditions which can be ameliorated by the inhibition of poly(ADP-ribose)polymerase (PARP), which method comprises administration to a patient in need thereof of an effective amount of a pharmaceutically acceptable salt of a compound of formula I or a composition comprising such a salt.

The PARP inhibitors of the present invention are useful for the treatment of the diseases specified in WO 2005/082368.

The compounds of the invention are useful for the treatment of inflammatory diseases, including conditions resulting from organ transplant rejection, such as; chronic inflammatory diseases of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung diseases such as asthma, adult respiratory distress syndrome, and chronic obstructive airway disease; inflammatory diseases of the eye including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney including uremic complications, glomerulonephritis and nephrosis; inflammatory diseases of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; diabetic complications, including, but not limited to, immune-complex vasculitis, systemic lupus erythematosus (SLE); inflammatory diseases of the heart such as cardiomyopathy, ischemic heart disease, hypercholesterolemia, and atherosclerosis; as well as various other diseases that can have significant inflammatory components, including preeclampsia, chronic liver failure, brain and spinal cord trauma and multiple organ dysfunction syndrome (MODS) (multiple organ failure (MOF)). The inflammatory disease can also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g. by a chemotherapeutic agent that is administered as a treatment for cancer.

Thus, the present invention provides a pharmaceutically acceptable salt of a compound of formula I for use in the manufacture of a medicament for treating or preventing inflammatory diseases.

The present invention also provides a method for the treatment or prevention of inflammatory diseases, which method comprises administration to a patient in need thereof of an effective amount of a pharmaceutically acceptable salt of a compound of formula I or a composition comprising such a salt.

The compounds of the instant invention may also be useful in the treatment or prevention of reperfusion injuries, resulting from naturally occurring episodes and during a surgical procedure, such as intestinal reperfusion injury; myocardial reperfusion injury; reperfusion injury resulting from cardiopulmonary bypass surgery, aortic aneurysm repair surgery, carotid endarterectomy surgery, or hemorrhagic shock; and reoxygenation injury resulting from transplantation of organs such as heart, lung, liver, kidney, pancreas, intestine, and cornea.

Thus, the present invention provides a pharmaceutically acceptable salt of a compound of formula I for use in the manufacture of a medicament for the treatment or prevention of reperfusion injuries.

The present invention also provides a method for the treatment or prevention of reperfusion injuries, which method comprises administration to a patient in need thereof of an effective amount of a pharmaceutically acceptable salt of a compound of formula I or a composition comprising such a salt.

The compounds of the instant invention may also be useful in the treatment or prevention of ischemic conditions, including those resulting from organ transplantation, such as stable angina, unstable angina, myocardial ischemia, hepatic ischemia, mesenteric artery ischemia, intestinal ischemia, critical limb ischemia, chronic critical limb ischemia, cerebral ischemia, acute cardiac ischemia, ischemia kidney disease, ischemic liver disease, ischemic retinal disorder, septic shock, and an ischemic disease of the central nervous system, such as stroke or cerebral ischemia.

Thus, the present invention provides a pharmaceutically acceptable salt of a compound of formula I for use in the manufacture of a medicament for the treatment or prevention of ischemic conditions.

The present invention also provides a method for the treatment or prevention of ischemic conditions, which method comprises administration to a patient in need thereof of an effective amount of a pharmaceutically acceptable salt of a compound of formula I or a composition comprising such a salt.

The present invention provides a pharmaceutically acceptable salt of a compound of formula I for use in the manufacture of a medicament for the treatment or prevention of stroke.

The present invention also provides a method for the treatment or prevention of stroke, which method comprises administration to a patient in need thereof of an effective amount of a pharmaceutically acceptable salt of a compound of formula I or a composition comprising such a salt.

The compounds of the instant invention may also be useful for the treatment or prevention of chronic or acute renal failure.

Thus, the present invention provides a pharmaceutically acceptable salt of a compound of formula I for use in the manufacture of a medicament for the treatment or prevention of renal failure.

The present invention also provides a method for the treatment or prevention of renal failure, which method comprises administration to a patient in need thereof of an effective amount of a pharmaceutically acceptable salt of a compound of formula I or a composition comprising such a salt.

The compounds of the instant invention may also be useful for the treatment or prevention of vascular diseases other than cardiovascular diseases, such as peripheral arterial occlusion, thromboangitis obliterans, Reynaud's disease and phenomenon, acrocyanosis, erythromelalgia, venous thrombosis, varicose veins, arteriovenous fistula, lymphedema and lipedema.

Thus, the present invention provides a pharmaceutically acceptable salt of a compound of formula I for use in the manufacture of a medicament for the treatment or prevention of vascular diseases other than cardiovascular diseases.

The present invention also provides a method for the treatment or prevention of vascular diseases other than cardiovascular diseases, which method comprises administration to a patient in need thereof of an effective amount of a pharmaceutically acceptable salt of a compound of formula I or a composition comprising such a salt.

The compounds of the instant invention may also be useful for the treatment or prevention of cardiovascular diseases such as chronic heart failure, atherosclerosis, congestive heart failure, circulatory shock, cardiomyopathy, cardiac transplant, myocardialinfarction, and a cardiac arrhythmia, such as atrial fibrillation, supraventricular tachycardia, atrial flutter, and paroxysmal atrial tachycardia.

Thus, the present invention provides a pharmaceutically acceptable salt of a compound of formula I for use in the manufacture of a medicament for the treatment or prevention of cardiovascular diseases.

The present invention also provides a method for the treatment or prevention of cardiovascular diseases, which method comprises administration to a patient in need thereof of an effective amount of a pharmaceutically acceptable salt of a compound of formula I or a composition comprising such a salt.

The compounds of this invention may also be useful for the treatment and prevention of diabetes mellitus, including Type I diabetes (Insulin Dependent Diabetes Mellitus), Type II diabetes (Non-Insulin Dependent Diabetes Mellitus), gestational diabetes, autoimmune diabetes, insulinopathies, diabetes due to pancreatic disease, diabetes associated with other endocrine diseases (such as Cushing's Syndrome, acromegaly, pheochromocytoma, glucagonoma, primary aldosteronism or somatostatinoma), Type A insulin resistance syndrome, Type B insulin resistance syndrome, lipatrophic diabetes, and diabetes induced by (3-cell toxins. The compounds of this invention may also be useful for the treatment or prevention of diabetic complications, such as diabetic cataract, glaucoma, retinopathy, nephropathy, (such asmicroaluminuria and progressive diabetic nephropathy), polyneuropathy, gangrene of the feet, atherosclerotic coronary arterial disease, peripheral arterial disease, nonketotic hyperglycemic-hyperosmolar coma, mononeuropathies, autonomic neuropathy, foot ulcers, joint problems, and a skin or mucous membrane complication (such as an infection, a shin spot, a candidal infection or necrobiosis lipoidica diabeticorumobesity), hyperlipidemia, hypertension, syndrome of insulin resistance, coronary artery disease, retinopathy, diabetic neuropathy, polyneuropathy, mononeuropathies, autonomic neuropathy, a foot ulcer, a joint problem, a fungal infection, a bacterial infection, and cardiomyopathy.

Thus, the present invention provides a pharmaceutically acceptable salt of a compound of formula I for use in the manufacture of a medicament for the treatment or prevention of diabetes.

The present invention also provides a method for the treatment or prevention of diabetes, which method comprises administration to a patient in need thereof of a pharmaceutically acceptable salt of an effective amount of a compound of formula I or a composition comprising such a salt.

The compounds of this invention may also be useful for the treatment or prevention of cancer including solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, skin cancer, melanoma, neuroblastoma and retinoblastoma; blood-borne cancers such as acute lymphoblastic leukemia ("ALL"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia and multiple myeloma; acute and chronic leukemias such as lymphoblastic, myelogenous, lymphocytic, myelocytic leukemias; Lymphomas such as Hodgkin's disease, non-Hodgkin's Lymphoma, Multiple myeloma, Waldenstrom's macroglobulinemia, Heavy chain disease and Polycythemia vera; CNS and brain cancers such as glioma, pilocytic astrocytoma, astrocytoma, anaplastic astrocytoma, glioblastoma multiforme, medulloblastoma, craniopharyngioma, ependymoma, pinealoma, hemangioblastoma, acoustic neuroma, oligodendroglioma, meningioma, vestibular schwannoma, adenoma, metastatic brain tumor, meningioma, spinal tumor and medulloblastoma.

Thus, the present invention provides a pharmaceutically acceptable salt of a compound of formula I for use in the manufacture of a medicament for the treatment or prevention of cancer.

The present invention also provides a method for the treatment or prevention of cancer, which method comprises administration to a patient in need thereof of an effective amount of a pharmaceutically acceptable salt of a compound of formula I or a composition comprising such a salt.

The compounds of the present invention may also be used for the treatment of cancer which is deficient in Homologous Recombination (HR) dependent DNA DSB repair activity (see WO 2006/021801).

The HR dependent DNA DSB repair pathway repairs double-strand breaks (DSBs) in DNA via homologous mechanisms to reform a continuous DNA helix (*Nat. Genet.* (2001) 27(3):247-254). The components of the HR dependent DNA DSB repair pathway include, but are not limited to, ATM (NM-000051), RAD51 (NM-002875), RAD51 L1 (NM-002877), RAD51 C (NM-002876), RAD51L3 (NM-002878), DMC1 (NM-007068), XRCC2 (NM7005431), XRCC3 (NM-005432), RAD52 (NM-002879), RAD54L (NM-003579), RAD54B (NM-012415), BRCA-1 (NM-007295), BRCA-2 (NM-000059), RAD50 (NM-005732), MREI 1A (NM-005590), NBS1 (NM-002485), ADPRT (PARP-1), ADPRTL2, (PARP02) CTPS, RPA, RPA1, RPA2, RPA3, XPD, ERCC1, XPF, MMS19, RAD51, RAD51p, RAD51C, RAD51D, DMC1, XRCCR, XRCC3, BRCA1, BRCA2, RAD52, RAD54, RAD50, MRE11, NB51, WRN, BLMKU70, RU80, ATM, ATRCHK1, CHK2, FANCA, FANCB, FANCC, FANCD1, FANCD2, FANCE, FANCF, FANCG, FANCC, FANCD1, FANCD2, FANCE, FANCF, FANCG, RAD1 and RAD9. Other proteins involved in the HR dependent DNA DSB repair pathway include regulatory factors such as EMSY (*Cell* (2003) 115:523-535).

A cancer which is deficient in HR dependent DNA DSB repair may comprise or consist of one or more cancer cells which have a reduced or abrogated ability to repair DNA DSBs through that pathway, relative to normal cells i.e. the activity of the HR dependent DNA DSB repair pathway may be reduced or abolished in the one or more cancer cells.

The activity of one or more components of the HR dependent DNA DSB repair pathway may be abolished in the one or more cancer cells of an individual having a cancer which is deficient in HR dependent DNA DSB repair. Components of the HR dependent DNA DSB repair pathway are well characterized in the art (see for example, *Science* (2001) 291: 1284-1289) and include the components listed above.

The present invention provides of a pharmaceutically acceptable salt of a compound of formula I for use in the manufacture of a medicament for the treatment or prevention of a cancer which is deficient in HR dependent DNA DSB repair activity.

The present invention also provides a method for the treatment or prevention of a cancer which is deficient in HR dependent DNA DSB repair activity, which method comprises administration to a patient in need thereof of a pharmaceutically acceptable salt of an effective amount of a compound of formula I or a composition comprising such a salt.

In an embodiment the cancer cells are deficient in the HR dependent DNA DSB repair activity of one or more phenotypes selected from ATM (NM-000051), RAD51 (NM-002875), RAD51L1 (NM-002877), RAD51 C (NM-002876), RAD51L3 (NM-002878), DMC1 (NM-007068), XRCC2 (NM7005431), XRCC3 (NM-005432), RAD52 (NM-002879), RAD54L (NM-003579), RAD54B (NM-012415), BRCA-1 (NM-007295), BRCA-2 (NM-000059), RAD50 (NM-005732), MREI 1A (NM-005590), NBS1 (NM-002485)), ADPRT (PARP-1), ADPRTL2, (PARP02) CTPS, RPA, RPA1, RPA2, RPA3, XPD, ERCC1, XPF, MMS19, RAD51, RAD51p, RAD51C, RAD51D, DMC1, XRCCR, XRCC3, BRCA1, BRCA2, RAD52, RAD54, RAD50, MRE11, NB51, WRN, BLMKU70, RU80, ATM, ATRCHK1, CHK2, FANCA, FANCB, FANCC, FANCD1, FANCD2, FANCE, FANCF, FANCG, FANCC, FANCD1, FANCD2, FANCE, FANCF, FANCG, RAD1 and RAD9.

In another embodiment, the cancer cells have a BRCA1 and/or a BRCA2 deficient phenotype. Cancer cells with this phenotype may be deficient in BRCA1 and/or BRCA2, i.e. expression and/or activity of BRCA-1 and/or BRCA-2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor (*Cell* (2003) 115:523-535).

BRCA-1 and BRCA-2 are known tumor suppressors whose wild-type alleles are frequently lost in tumors of heterozygous carriers (*Oncogene*, (2002) 21(58):8981-93; *Trends Mol Med.*, (2002) 8(12):571-6). The association of BRCA-1 and/or BRCA-2 mutations with breast cancer has been well-characterized (*Exp Clin Cancer Res.*, (2002) 21 (3 Suppl):9-12). Amplification of the EMSY gene, which encodes a BRCA-2 binding factor, is also known to be associated with breast and ovarian cancer. Carriers of mutations in BRCA-1 and/or BRCA-2 are also at elevated risk of cancer of the ovary, prostate and pancreas. The detection of variation in BRCA-1 and BRCA-2 is well-known in the art and is described, for example in EP 699 754, EP 705 903, *Genet. Test* (1992) 1:75-83; *Cancer Treat Res* (2002) 107:29-59; *Neoplasm* (2003) 50(4):246-50; *Ceska Gynekol* (2003) 68(1):11-16). Determination of amplification of the BRCA-2 binding factor EMSY is described in *Cell* 115:523-535. PARP inhibitors have been demonstrated as being useful for the specific killing of BRCA-1 and BRCA-2 deficient tumors (*Nature* (2005) 434:913-916 and 917-920).

Thus, the present invention provides a pharmaceutically acceptable salt of a compound of formula I for use in the manufacture of a medicament for the treatment or prevention of BRCA-1 or BRCA-2 deficient tumors.

The present invention also provides a method for the treatment or prevention of BRCA-1 or BRCA-2 deficient tumors, which method comprises administration to a patient in need thereof of an effective amount of a pharmaceutically acceptable salt of a compound of formula I or a composition comprising such a salt.

In an embodiment, the PARP inhibitors of the present can be used in prophylactic therapy for elimination of BRCA2-deficient cells (see, *Cancer Res*. (2005) 65:10145).

The compounds of this invention may be useful for the treatment or prevention of neurodegenerative diseases, including, polyglutamine-expansion-related neurodegeneration, Huntington's disease, Kennedy's disease, spinocerebellar ataxia, dentatorubral-pallidoluysian atrophy (DRPLA), protein-aggregation-related neurodegeneration, Machado-Joseph's disease, Alzheimer's disease, Parkinson's disease, amyotrophic lateral sclerosis, spongiform encephalopathy, a prion-related disease and multiple sclerosis (MS).

Thus, the present invention provides a pharmaceutically acceptable salt of a compound of formula I for use in the manufacture of a medicament for treating or preventing neurodegenerative diseases.

The present invention also provides a method for treating or preventing neurodegenerative diseases, which method comprises administration to a patient in need thereof of an effective amount of a pharmaceutically acceptable salt of a compound of formula I or a composition comprising such a salt.

The compounds of the present invention may also be useful for the treatment or prevention of retroviral infection (U.S. Pat. No. 5,652,260), retinal damage (*Curr. Eye Res.* (2004), 29:403), skin senescence and UV-induced skin damage (U.S. Pat. No. 5,589,483 and *Biochem. Pharmacol* (2002) 63:921).

The compounds of the invention are useful for the treatment or prevention of premature aging and postponing the onset of age-related cellular dysfunction (*Pharmacological Research* (2005) 52:93-99).

The compounds of this invention may be administered to mammals, preferably humans, either alone or in combination with pharmaceutically acceptable carriers, excipients, diluents, adjuvants, fillers, buffers, stabilisers, preservatives, lubricants, in a pharmaceutical composition, according to standard pharmaceutical practice.

The compounds of this invention may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, (e.g. by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal); and by implant of a depot (e.g. subcutaneously or intramuscularly).

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium croscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the instant compounds are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a subject, the selected dosage level will depend on a variety of factors including, but not limited to, the activity of the particular compound, the severity of the individuals symptoms, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

The instant compounds are also useful in combination with anti-cancer agents or chemotherapeutic agents.

The compounds of this invention may be useful as chemo- and radiosensitizers for cancer treatment. They are useful for the treatment of mammals who have previously undergone or are presently undergoing treatment for cancer. Such previous treatments include prior chemotherapy, radiation therapy, surgery or immunotherapy, such as cancer vaccines.

Thus, the present invention provides a combination of a pharmaceutically acceptable salt of a compound of formula I and an anti-cancer agent for simultaneous, separate or sequential administration.

The present invention also provides a combination of a pharmaceutically acceptable salt of a compound of formula I, radiation therapy and another chemotherapeutic agent for simultaneous, separate or sequential administration.

The present invention also provides a pharmaceutically acceptable salt of a compound of formula I for use in the manufacture of a medicament for use as an adjunct in cancer therapy or for potentiating tumor cells by combination with ionizing radiation or chemotherapeutic agents.

The present invention also provides the use of a pharmaceutically acceptable salt of a compound of formula I in the manufacture of a medicament for use as an adjunct in cancer therapy or for potentiating tumor cells by combination with ionizing radiation and other chemotherapeutic agents. The compounds can also be used in combination with ionizing radiation and other chemotherapeutic agents.

The present invention also provides a method of chemotherapy or radiotherapy, which method comprises administration to a patient in need thereof of an effective amount of a pharmaceutically acceptable salt of a compound of formula I or a composition comprising such a a salt in combination with ionizing radiation or chemotherapeutic agents. The compounds can also be administered in combination with ionizing radiation and other chemotherapeutic agents.

In combination therapy, the compounds of this invention can be administered prior to (e. g., 5 minutes, 15 minutes, 30 minutes, 45 minutes, 1 hour, 2 hours, 4 hours, 6 hours, 12 hours, 24 hours, 48, hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the other anticancer agent to a subject in need thereof. In various embodiments the instant compounds and another anticancer agent are administered 1 minute apart, 10 minutes apart, 30 minutes apart, less than 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart, or no more than 48 hours apart.

The compounds of this invention and the other anticancer agent can act additively or synergistically. A synergistic combination of the present compounds and another anticancer agent might allow the use of lower dosages of one or both of these agents and/or less frequent dosages of one or both of the instant compounds and other anticancer agents and/or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

Examples of cancer agents or chemotherapeutic agents for use in combination with the compounds of the present invention can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: HDAC inhibitors, estrogen receptor modulators, androgen receptor modulators, retinoid receptor modulators, cytotoxic/cytostatic agents, antiproliferative agents, prenyl-protein transferase inhibitors, HMG-CoA reductase inhibitors, HIV protease inhibitors, reverse transcriptase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

Examples of "HDAC inhibitors" include suberoylanilide hydroxamic acid (SAHA), LAQ824, LBH589, PXD101, MS275, FK228, valproic acid, butyric acid and CI-994.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites, biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, cyclophosphamide, chlorambucil carmustine (BCNU), lomustine (CCNU), busulfan, treosulfan, sertenef, cachectin, ifosfamide, tasonermin, lonidamine, carboplatin, altretamine, prednimustine, dibromodulcitol, ranimustine, fotemustine, nedaplatin, aroplatin, oxaliplatin, temozolomide, methyl methanesulfonate, procarbazine, dacarbazine, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, doxorubicin, epirubicin, pirarubicin, antineoplaston, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulphonyl-daunorubicin (see WO 00/50032). Further examples include Raf kinase inhibitors (such as Bay43-9006) and mTOR inhibitors (such as Wyeth's CCI-779 and Ariad AP23573). Further examples are inhibitors of PI3K (for example LY294002).

In an embodiment the compounds of this invention can be used in combination with alkylating agents.

Examples of alkylating agents include but are not limited to, nitrogen mustards: cyclophosphamide, ifosfamide, trofosfamide and chlorambucil; nitrosoureas: carmustine (BCNU) and lomustine (CCNU); alkylsulphonates: busulfan and treosulfan; triazenes: dacarbazine, procarbazine and temozolomide; platinum containing complexes: cisplatin, carboplatin, aroplatin and oxaliplatin.

In an embodiment, the alkylating agent is dacarbazine. Dacarbazine can be administered to a subject at dosages ranging from about 150 mg/m2 (of a subject's body surface area) to about 250 mg/m2. In another embodiment, dacarbazine is administered intravenously to a subject once per day for five consecutive days at a dose ranging from about 150 mg/m2 to about 250 mg/m2.

In an embodiment, the alkylating agent is procarbazine. Procarbazine can be administered to a subject at dosages ranging from about 50 mg/m2 (of a subject's body surface area) to about 100 mg/m2. In another embodiment, procarbazine is administered intravenously to a subject once per day for five consecutive days at a dose ranging from about 50 mg/m2 to about 100 mg/m2.

In an embodiment, the alkylating agent is temozoloamide. Temozolomide can be administered to a subject at dosages ranging from about 150 mg/m2 (of a subject's body surface area) to about 200 mg/m2. In another embodiment, temozolomide is administered orally to an animal once per day for five consecutive days at a dose ranging from about 150 mg/m2 to about 200 mg/m2.

Examples of anti-mitotic agents include: allocolchicine, halichondrin B, colchicine, colchicine derivative, dolstatin 10, maytansine, rhizoxin, thiocolchicine and trityl cysteine.

An example of a hypoxia activatable compound is tirapazamine.

Examples of proteasome inhibitors include but are not limited to lactacystin, bortezomib, epoxomicin and peptide aldehydes such as MG 132, MG 115 and PSI.

Examples of microtubule inhibitors/microtubule-stabilising agents include paclitaxel, vindesine sulfate, vincristine, vinblastine, vinorelbine, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, exatecan, gimetecan, diflomotecan, silyl-camptothecins, 9-aminocamptothecin, camptothecin, crisnatol, mitomycin C, 6-ethoxypropionyl-3', 4'-O-exo-benzylidene-chartreusin, 9-methoxy-N,N-dimethyl-5-nitropyrazolo[3,4,5-k1]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1, 2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7) naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna; non-camptothecin topoisomerase-1 inhibitors such as indolocarbazoles; and dual topoisomerase-1 and II inhibitors such as benzophenazines, XR20 115761MLN 576 and benzopyridoindoles.

In an embodiment, the topoisomerase inhibitor is irinotecan. Irinotecan can be administered to a subject at dosages ranging from about 50 mg/m2 (of a subject's body surface area) to about 150 mg/m2. In another embodiment, irinotecan is administered intravenously to a subject once per day for five consecutive days at a dose ranging from about 50 mg/m2 to about 150 mg/m2 on days 1-5, then again intravenously once per day for five consecutive days on days 28-32 at a dose ranging from about 50 mg/m2 to about 150 mg/m2, then again intravenously once per day for five consecutive days on days 55-59 at a dose ranging from about 50 mg/m2 to about 150 mg/m2.

Examples of inhibitors of mitotic kinesins, and in particular the human mitotic kinesin KSP, are described in PCT Publications WO 01/30768, WO 01/98278, WO 02/056880, WO 03/050,064, WO 03/050,122, WO 03/049,527, WO 03/049,679, WO 03/049,678, WO 03/039460, WO 03/079973, WO 03/099211, WO 2004/039774, WO 03/105855, WO 03/106417, WO 2004/087050, WO 2004/058700, WO 2004/058148 and WO 2004/037171 and US 2004/132830 and US 2004/132719. In an embodiment inhibitors of mitotic kinesins include, but are not limited to, inhibitors of KSP, inhibitors of MKLP1, inhibitors of CENP-E, inhibitors of MCAK, inhibitors of Kif14, inhibitors of Mphosph1 and inhibitors of Rab6-KIFL.

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer (1999), 35(9):1394-1401.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS (1992) 89:7384; JNCI (1982) 69:475; Arch. Opthalmol. (1990) 108: 573; Anat. Rec. (1994) 238:68; FEBS Letters (1995) 372:83; Clin, Orthop. (1995) 313:76; J. Mol. Endocrinol. (1996) 16:107; Jpn. J. Pharmacol. (1997) 75:105; Cancer Res. (1997) 57:1625 (1997); Cell (1998) 93:705; Intl. J. Mol. Med. (1998) 2:715; J. Biol. Chem. (1999) 274:9116)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see J. Lab. Clin. Med. (1985) 105:141-145), and antibodies to VEGF (see Nature Biotechnology (1999) 17:963-968; Kim et al (1993) Nature 362:841-844; WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. (2000) 38:679-692). Examples of such agents that modulate or inhibit the coagulation and fibrinolysis pathways include, but are not limited to, heparin (see Thromb. Haemost. (1998) 80:10-23), low molecular weight heparins and carboxypeptidase U inhibitors (also known as inhibitors of active thrombin activatable fibrinolysis inhibitor [TAFIa]) (see Thrombosis Res. (2001) 101:329-354). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, staurosporin, flavopiridol, CYC202 (Cyclacel) and BMS-387032.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR (for example those disclosed in WO 03/059951), inhibitors of cytokine receptors, inhibitors of MET, inhibitors of PI3K (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include activators of TNF receptor family members (including the TRAIL receptors).

In an embodiment the compounds of the present invention are useful for treating cancer in combination with one or more, particularly one, two or three agents selected from temozolomide, cisplatin, carboplatin, oxaliplatin, irinotecan and topotecan.

A compound of the instant invention may also be useful for treating cancer in combination with any one or more of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorine, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®); zoledronate (Zometa®); nilotinib (Tasigna®) and dasatinib (Sprycel®).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633, 272, and U.S. Pat. No. 5,932,598, all of which are hereby incorporated by reference.

Inhibitors of COX-2 that are particularly useful in the instant method of treatment are 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpimase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\beta_5\alpha_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-k1]pyrrolo [3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

In an embodiment, the compounds of the present invention are useful for the treatment or prevention of the appearance of necrosis induced by selective N3-adenine methylating agents such as $MeOSO_2(CH_2)$-lexitropsin (Me-Lex).

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors β and δ. The expression of PPAR-γ on endothelial cells and its involvement in angiogenesis has been reported in the literature (see *J. Cardiovasc. Pharmacol.* (1998) 31:909-913; *J. Biol. Chem.* (1999) 274: 9116-9121; *Invest. Opthalmol. Vis. Sci.* (2000) 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* (2001) 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with antiviral agents (such as nucleoside analogs including ganciclovir for the treatment of cancer. See WO 98/04290.

Another embodiment of the instant invention is the use of the presently disclosed compounds in combination with gene therapy for the treatment of cancer. For an overview of genetic strategies to treating cancer see Hall et al (*Am J Hum Genet* (1997) 61:785-789) and Kufe et al (*Cancer Medicine*, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August (1998) 5(8):1105-13), and interferon gamma (*J Immunol* (2000) 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853, verapamil and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, $GABA_B$ receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707

006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

Thus, the scope of the instant invention encompasses the use of the instantly claimed compounds in combination with ionizing radiation and/or in combination with a second compound selected from: HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interferes with a cell cycle checkpoint, an apoptosis inducing agent and a bisphosphonate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treatment" refers to the treatment of a mammal afflicted with a pathological condition and refers to an effect that alleviates the condition by killing the cancerous cells, but also to an effect that results in the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The term "adjunct" refers to the use of compounds in conjunction with known therapeutic means. Such means include cytotoxic regimes of drugs and/or ionising radiation as used in the treatment of different cancer types. In particular, the active compounds are known to potentiate the actions of a number of cancer chemotherapy treatments, which include the topoisomerase class of poisons (e.g. topotecan, irinotecan, rubitecan), most of the known alkylating agents (e.g. DTIC, temozolamide) and platinum based drugs (e.g. carboplatin, cisplatin) used in treating cancer.

Also included in the scope of the claims is a method of treating cancer that comprises administering a therapeutically effective amount of a pharmaceutically acceptable salt of a compound of Formula I in combination with radiation therapy and/or in combination with a compound selected from: HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interferes with a cell cycle checkpoint, an apoptosis inducing agent and a bisphosphonate.

These and other aspects of the invention will be apparent from the teachings contained herein.

Abbreviations Used in the Description of the Chemistry and in the Examples that Follow are:

AcCl (acetyl chloride); (BzO)$_2$ (benzoyl peroxide); CDCl$_3$ (deutrated chloroform); DCM (dichloromethane); DMF (dimethylformamide); DMSO (dimethyl sulfoxide); eq. (equivalent); ES (electrospray); EtOAc (ethyl acetate); EtOH (ethanol); mol. sieves (molecular sieves); MeCN (acetonitrile); MeOH (methanol); MS (mass spectrometry); MW (microwave); NBS (N-bromosuccinimide); NMMO (N-methylmorpholine-N-oxide); NMR (nuclear magnetic resonance); Pcol (column pressure); iPrOH (isopropanol); RH (relative humidity); RT (room temperature); sat. aq. (saturated aqueous); SiO$_2$ (silica gel); and THF (tetrahydrofuran). IST ISOLUTE® SPE column SCX (International Sorbent Technology ISOLUTE® Solid Phase Extraction column cationic exchange resin); SFC (supercritical fluid chromatography); TBTU O-(1H-benzotriazol-1-yl)-N,N,N',N'-tetramethyluronium tetrafluoroborate; Tcol (column temperature); TFA (trifluoroacetic acid); and TLC (thin layer chromatography).

Where the synthesis of intermediates and starting materials is not described, these compounds are commercially available or can be made from commercially available compounds by standard methods or by extension of the synthesis above, schemes and Examples herein.

During any of the synthetic sequences described herein it may be necessary and/or desirable to protect sensitive or reactive groups on any of the molecules concerned. This may be achieved by means of conventional protecting groups, such as those described in *Protecting Groups in Organic Synthesis,* 3rd Edition, Greene, T. W. and Wuts, P. G. M.; Wiley Interscience, 1999 and Kocienski, P. J. *Protecting Groups*, Thieme, 1994. The protecting groups may be removed at a convenient subsequent stage using methods known from the art. For example, when the Boc (tert-butoxycarbonyl) or benzylcarbonyl protecting group is present, it may be removed by the addition of solvents such as TFA, DCM and/or MeCN at about room temperature. The compound may also be hydrogenated using standard methods, such as treating with a catalyst such as Pd/C, in a solvent such as methanol under a hydrogen atmosphere. EtOAc in the presence of HCl and 1,4-dioxane may also be added to remove the Boc or benzylcarbonyl protecting group, at about room temperature.

When the compounds of the present invention have chiral centres, the enantiomers may be separated from the racemic mixtures by standard separating methods such as using SFC, chiral HPLC or resolution with chiral acids. The separation can be carried out at any step of the process for making the compounds of formula I. Thus, separation can be carried out at the final step, or alternatively intermediates can be separated and then particular enantiomers utilized in subsequent reactions to produce the desired products.

PARP-1 SPA Assay

The exemplified compounds described herein were tested in this assay and were found to have an IC$_{50}$ value of less than 5 μM, particularly less than 50 nM.

Working Reagents

Assay buffer: 100 mM Tris pH 8, 4 mM MgCl$_2$, 4 mM Spermine, 200 mM KCl, 0.04% Nonidet P-40.

Enzyme Mix: Assay buffer (12.5 ul), 100 mM DTT (0.5 ul), PARP-1 (5 nM, Trevigen 4668-500-01), H$_2$O (to 35 ul).

Nicotinamide-adenine dinucleotide (NAD)/DNA Mix: [$^3$H-NAD] (250 uCi/ml, 0.4 ul, Perkin-Elmer NET-443H), NAD (1.5 mM, 0.05 ul, SIGMA N-1511), Biotinylated-NAD (250 uM, 0.03 ul, Trevigen 4670-500-01), Activated calf thymus (1 mg/ml, 0.05 ul, Amersham Biosciences 27-4575), H$_2$O (to 10 ul).

Developing Mix: Streptavidin SPA beads (5 mg/ml, Amersham Biosciences RPNQ 0007) dissolved in 500 mM EDTA.

Experimental Design

The reaction is performed in 96-well microplate with a final volume of 50 uL/well. Add 5 ul 5% DMSO/compound solution, add enzyme mix (35 ul), start the reaction by adding NAD/DNA mix (10 uL) and incubate for 2 hrs at RT. Stop the reaction by adding developing mix (25 ul) and incubate 15 min at RT. Measure using a Packard TOP COUNT instrument.

Proliferation Assay in BRCA-1 Silenced HeLa Cells

Abbreviations

IMDM (Iscove's Modified Dulbecco's Media); RPMI (Roswell Park Memorial Institute Media); MOI (multiplicity of infection); GFP (green fluorescent protein); PBS (Phosphate Buffered Saline); FCS (fetal calf serum); and DMEM (Dulbecco's Modified Eagle's Medium).

Compounds of the present invention were also tested in an anti-proliferative assay in matched pair BRCA1 wt and BRCA1-(shRNA) HeLa cells. The assay shows that PARP inhibitors are able to show selectivity with growth inhibition of the BRCA deficient cells. The compounds showed CC$_{50}$'s less than 5 μM in BRCA1 deficient cells and a greater than 10 fold selectivity over the BRCA proficient cells.

The assay is based on the ability of living cells to convert a redox dye (resazurin) into a fluorescent end product (resofurin). The amount of resofurin produced is directly proportional to the cell number.

Cell Lines:

HeLa shBRCA1-GFP—These are HeLa cells transduced at an MOI of 100 with a Lentivirus containing a shRNA against BRCA-1 and an expression cassette for GFP. BRCA-1 silencing is more than 80% as assessed by Taqman analysis and the cells stably express GFP.

HeLa THM-GFP—These are HeLa cells transduced at an MOI of 100 with a control vector not expressing any shRNA.

Protocol

Seed 300 cell/well in 96 wells viewplate black in 90 μl culture Medium*:
Incubate 4 hours at 37° C., 5% CO$_2$
Add 10 μl/well of 10× compound (5% DMSO in H$_2$O)
Incubate for 168 hours at 37° C., 5% CO$_2$
Add 10 μl of Celltiter Blue solution (Promega, G8081) pre-diluted 1:1 in PBS 1×
Incubate the mixture for 45' at 37° C., 5% CO$_2$
Incubate 15' at RT in the dark
Read plate at fluorimeter ex: 550 nm; em: 590 nm

*Culture Medium: DMEM (GIBCO, 41966-029), 10% FCS (GIBCO, 10106-169), 0.1 mg/ml Penicillin-Streptomycin (GIBCO, 15140-114), 2 mM L-Glutamine (GIBCO, 3042190)

Proliferation Assay in Naturally BRCA Deficient Cells Lines

Compounds of the present invention were also demonstrated to inhibit the proliferation of naturally BRCA-1

(MDA-MB-436) and BRCA-2 (CAPAN-1) deficient cell lines with $CC_{50}$'s less than 5 micromolar.

Proliferation Assay

Cells are seeded in a 96-well plate at 700 cells/well in 100 ul of the appropriate medium/well.* The following day, serial dilutions of the compound are added in a final volume of 200 μl/well. Each dilution is assayed in triplicates.

Six days later, cell viability is estimated using CellTiter-Blue Cell Viability Assay according to the manufacturer instructions (Promega). Plates are read at the Fusion Alpha microplate reader (Packard Bioscience).

For low-proliferating cell lines (i.e. CAPAN-1), proliferation is assayed 14 days after adding the compounds and changing the medium once at day 7 (170 μl of medium per well are aspirated and replaced with 170 μl fresh medium containing the compounds).

*Culture Medium:
MDA-MB-436: RPMI (GIBCO), 10% FBS (5% $CO_2$)
CAPAN-1: IMDM (GIBCO), 20% FBS (5% $CO_2$)

Compounds tested in an oncology in vivo model showed a significant level of activity.

PREPARATIVE EXAMPLES

Example A

2-Phenyl-2H-indazole-7-carboxamide (A6)

Step 1: Methyl 3-methyl-2-nitrobenzoate (A1)

To a suspension of 3-methyl-2-nitro-benzoic acid (1.0 eq.) in MeOH (0.4 M) at 0° C. was added dropwise AcCl (3.0 eq.). The reaction mixture was stirred for 20 hr at reflux. The solvent was reduced in vacuo and the residue was dissolved in EtOAc and washed several times with sat. aq. $NaHCO_3$ solution, brine and dried ($Na_2SO_4$). Evaporation of the solvent gave (A1) as a white solid which was used in the next step without further purification. $^1$H NMR (400 MHz, $CDCl_3$, 300K) δ 7.86 (1H, d, J=7.5 Hz), 7.53-7.42 (2H, m), 3.89 (3H, s), 2.36 (3H, s). MS (ES) $C_9H_9NO_4$ requires: 195. found: 218 $(M+Na)^+$.

Step 2: Methyl 3-(bromomethyl)-2-nitrobenzoate (A2)

A mixture of (A1) (1.0 eq.), $(BzO)_2$ (0.06 eq.) and NBS (1.18 eq.) in $CCl_4$ (0.2 M, with respect to A1) was heated at reflux under $N_2$ atmosphere for 12 hr. The mixture was cooled to RT, diluted with DCM, concentrated under reduced pressure whilst dry loading onto $SiO_2$. The residue was purified by flash column chromatography on $SiO_2$ using 10:90 EtOAc/Petroleum ether to yield the desired (A2) as a white solid. $^1$H NMR (400 MHz, $CDCl_3$, 300K) δ 7.93 (1H, d, J=7.7 Hz), 7.72 (1H, d, J=7.7 Hz), 7.57 (1H, t, J=7.7 Hz), 4.43 (2H, s), 3.88 (3H, s). MS (ES) $C_9H_8BrNO_4$ requires: 273:275. found: 242:244 $(M-MeO)^+$, 227:229 $(M-NO_2)^+$.

Step 3: Methyl 3-formyl-2-nitrobenzoate (A3)

To a mixture of (A2) (1.0 eq.) and 4 Å mol. sieves in MeCN (0.2M) at RT was added NMMO (2.0 eq.) and the reaction mixture was stirred for 1.5 hr under $N_2$ atmosphere. Then, the mixture was diluted with EtOAc, filtered and the filtrate was washed with $H_2O$, 1N HCl, brine and dried ($Na_2SO_4$). Evaporation of the solvent gave (A3) as a white solid which was used in the next step without further purification. $^1$H NMR (400 MHz, $CDCl_3$, 300K) δ 9.96 (1H, s), 8.26 (1H, d, J=7.9 Hz), 8.18 (1H, d, J=7.9 Hz), 7.77 (1H, t, J=7.9 Hz), 3.93 (3H, s). MS (ES) $C_9H_7NO_5$ requires: 209. found: 208 $(M-H)^-$.

Step 4: Methyl 2-nitro-3-[(phenylimino)methyl]benzoate (A4)

A mixture of (A3) (1.0 eq.) and aniline (1.05 eq.) in EtOH (0.2 M) was stirred at reflux under $N_2$ atmosphere for 2 hr until TLC revealed completation of the reaction (Hexane/EtOAc=75:25). Evaporation of the solvent gave (A4) as a white solid which was used in the next step without further purification. $^1$H NMR (400 MHz, $CDCl_3$, 300K) δ 8.51 (1H, d, J=7.3 Hz), 8.41 (1H, s), 8.11 (1H, d, J=7.8 Hz), 7.67 (1H, t, J=7.8 Hz), 7.43 (2H, t, J=7.8 Hz), 7.31 (1H, t, J=7.3 Hz), 7.16 (2H, d, J=7.8 Hz), 3.94 (3H, s).

Step 5: Methyl 2-phenyl-2H-indazole-7-carboxylate (A5)

A mixture of (A4) (1.0 eq.) and $NaN_3$ (1.05 eq.) in dry DMF (0.3 M) was stirred at 90° C. overnight under $N_2$ atmosphere. The crude was reduced in vacuo and the residue purified by flash column chromatography on silica using a gradient of EtOAc/Petroleum ether from 10:90 to 40:60 to yield the desired (A5) as a brown oil. $^1$H NMR (400 MHz, $CDCl_3$, 300K) δ 8.50 (1H, s), 8.12 (1H, d, J=7.0 Hz), 7.96-7.90 (3H, m), 7.49 (2H, t, J=7.6 Hz), 7.38 (1H, t, J=7.4 Hz), 7.15 (1H, t, J=7.4 Hz), 4.03 (3H, s). MS (ES) $C_{15}H_{12}N_2O_2$ requires: 252. found: 253 $(M+H)^+$.

Step 6: 2-Phenyl-2H-indazole-7-carboxamide (A6)

The ester (A5) was heated in a mixture of THF and 32% aq. $NH_3$ solution at 70° C. overnight in a sealed tube. The solvents were reduced in vacuo and the residue purified by flash column chromatography on silica using a gradient of EtOAc/Petroleum ether from 30:70 to 50:50 to yield the desired (A6) as white solid. $^1$H NMR (400 MHz, DMSO, 300K) δ 9.33 (1H, s), 8.56 (1H, bs), 8.16 (2H, d, J=7.9 Hz), 8.08-8.00 (2H, m), 7.88 (1H, bs), 7.63 (2H, t, J=7.7 Hz), 7.50 (1H, t, 7.4 Hz), 7.27 (1H, t, J=7.9 Hz). MS (ES) $C_{14}H_{11}N_3O$ requires: 237. found: 238 $(M+H)^+$.

Example B

3-{4-[7-(Aminocarbonyl)-2H-indazol-2-yl]phenyl}piperidinium chloride (B4)

Step 1: tert-Butyl 3-[4-({-[3-(methoxycarbonyl)-2-nitrophenyl]methylene}amino) phenyl]piperidine-1-carboxylate (B1)

(B1) was prepared following the general procedure reported for Example A step 4 using A3 and tert-butyl 3-(4-aminophenyl)piperidine-1-carboxylate until TLC revealed completion of the reaction (Petroleum ether:EtOAc=4:1) and was used in the next step without further purification.

Step 2: Methyl 2-{4-[1-(tert-butoxycarbonyl)piperidin-3-yl]phenyl}-2H-indazole-7-carboxylate (B2)

(B2) was prepared following the general procedure reported for Example A step 5 and the crude was purified by flash column chromatography on silica using a gradient of 20-40% EtOAc/Petroleum ether to yield the desired (B2) as a yellow solid. $^1$H NMR (400 MHz, $CDCl_3$, 300K) δ 8.51 (1H, s), 8.13 (1H, d, J=7.1 Hz), 7.95 (1H, d, J=8.3 Hz), 7.91 (2H, d, J=8.4 Hz), 7.39 (2H, d, J=8.4 Hz), 7.18 (1H, t, J=7.2 Hz), 4.30-4.10 (2H, m), 4.00 (3H, s), 2.85-2.70 (3H, m), 2.11-2.03 (1H, m), 1.83-1.75 (1H, m), 1.73-1.53 (2H, m overlapped to $H_2O$ signal), 1.48 (9H, s). MS (ES) $C_{25}H_{29}N_3O_4$ requires: 435. found: 436 $(M+H)^+$.

Step 3: tert-Butyl 3-{4-[7-(aminocarbonyl)-2H-indazol-2-yl]phenyl}piperidine-1-carboxylate (B3)

(B2) was heated in 7N $NH_3$ in MeOH (0.1 M) in a sealed tube for 2 days at 60° C. The solvents were reduced in vacuo and the crude product was purified by trituration with $Et_2O$ to give the desired (B3) as a yellow solid. $^1$H NMR (400 MHz, $CDCl_3$, 300K) δ 9.04 (1H, br. s), 8.51 (1H, s), 8.31 (1H, d, J=6.8 Hz), 7.91 (1H, d, J=8.3 Hz), 7.84 (2H, d, J=8.2 Hz), 7.42 (2H, d, J=8.2 Hz), 7.31-7.22 (1H, m overlapped to $CDCl_3$ signal), 5.95 (1H, br. s), 4.40-4.05 (2H, m), 2.90-2.70 (3H, m), 2.15-2.00 (1H, m), 1.85-1.75 (1H, m), 1.75-1.50 (2H, m overlapped to $H_2O$ signal), 1.48 (9H, s). MS (ES) $C_{24}H_{28}N_4O_3$ requires: 420. found: 421 $(M+H)^+$.

Step 4: 3-{4-[7-(Aminocarbonyl)-2H-indazol-2-yl]phenyl}piperidinium chloride (B4)

To a stirred solution of (B3) (1.0 eq.) in EtOAc (0.2M) 4N HCl/1,4-dioxane solution (10.0 eq.) was added and the reaction mixture was stirred at RT for 3 h. Solvent was evaporated under reduced pressure and the crude product purified by trituration with $Et_2O$ to yield the desired (B4) as a yellow solid. $^1$H NMR (400 MHz, DMSO-d6, 300K) δ 9.32 (1H, s), 9.12 (1H, br. s), 8.87 (1H, br. s), 8.55 (1H, br. s), 8.13 (2H, d, J=8.6 Hz), 8.06 (1H, J=7.0 Hz), 8.02 (1H, d, J=8.4 Hz), 7.89 (1H, br. s), 7.55 (2H, d, J=8.6 Hz), 7.27 (1H, dd, J=8.4, 7.0 Hz), 3.43-3.27 (2H, m), 3.17-3.03 (2H, m), 3.00-2.85 (1H, m), 2.00-1.70 (4H, m). MS (ES) $C_{19}H_{21}ClN_4O$ requires: 320. found: 321 $(M+H)^+$.

Example C

2-{4-[(3R)-Piperidin-3-yl]phenyl}-2H-indazole-7-carboxamide (C1) & 2-{4[(3S)-Piperidin-3-yl]phenyl}-2H-indazole-7-carboxamide (C2)

Example B, B4 was separated by chiral SFC (column: Chiralpak AS-H, 1×25 mm, flow: 10 ml/min, $T_{col}$: 35° C., $P_{col}$: 100 bar, modifier: 55% ($^i$PrOH+4% $Et_2NH$)), using $CO_2$ as supercritic eluent, affording both pure enantiomers.

The first eluted enantiomer (C1), retention time (SFC): 4.80 min, was obtained as a white powder. $^1$H NMR (400 MHz, DMSO-d6, 300K) δ 9.28 (s, 1H), 8.57 (br. s, 1H), 8.06 (d, 2H, J=7.2 Hz), 8.04 (d, 2H, J=8.4 Hz), 7.88 (br. s, 1H), 7.49 (d, 2H, J=8.4 Hz), 7.27 (dd, 1H, J=8.4, 7.2 Hz), 3.08-2.94 (m, 2H), 2.77-2.67 (m, 1H), 2.64-2.52 (m, 1H), 1.98-1.90 (m, 1H), 1.75-1.47 (m, 4H). MS (ES) $C_{19}H_{20}N_4O$ requires: 320. found: 321 $(M+H)^+$. The free base was converted to (3R)-3-{4-[7-(aminocarbonyl)-2H-indazol-2-yl]phenyl}piperidinium chloride and the optical rotation measured: $[\alpha]^{20}_D$=+133.3 (c 0.15, MeOH).

The second eluted enantiomer (C2), retention time (SFC): 6.51 min, was obtained as a white powder. $^1$H NMR (400 MHz, DMSO-d6, 300K) δ 9.28 (s, 1H), 8.57 (br. s, 1H), 8.06 (d, 2H, J=7.2 Hz), 8.04 (d, 2H, J=8.4 Hz), 7.88 (br. s, 1H), 7.49 (d, 2H, J=8.4 Hz), 7.27 (dd, 1H, J=8.4, 7.2 Hz), 3.08-2.94 (m, 2H), 2.77-2.67 (m, 1H), 2.64-2.52 (m, 1H), 1.98-1.90 (m, 1H), 1.75-1.47 (m, 4H). MS (ES) $C_{19}H_{20}N_4O$ requires: 320. found: 321 $(M+H)^+$. The free base was converted to (3S)-3-{4-[7-(aminocarbonyl)-2H-indazol-2-yl]phenyl}piperidinium chloride and the optical rotation measured: $[\alpha]^{20}_D$=−137.9 (c 0.145, MeOH).

REPRESENTATIVE EXAMPLES

Example 1

(3S)-3-{4-[7-(Aminocarbonyl)-2H-indazol-2-yl]phenyl}piperidinium 4-methylbenzenesulfonate (D4)

Step 1: tert-butyl(3S)-3-[4-({(IE)-[3-(methoxycarbonyl)-2-nitrophenyl]methylene}amino)phenyl]piperidine-1-carboxylate (D1)

(D1) was prepared from Example A, A3 and tert-butyl (3S)-3-(4-aminophenyl)piperidine-1-carboxylate (prepared by the resolution of 3-(4-aminophenyl)-piperidine with 2 equivalents of L-Dibenzoyl tartaric acid in MeOH and subsequent Boc-protection) as described in Example B, B1.

Step 2: 2-{4-[(3S)-1-(tert-butoxycarbonyl)piperidin-3-yl]phenyl}-2H-indazole-7-carboxylic acid (D2)

(D1) (1 eq.) and sodium azide (1 eq.) were slurried in DMF (0.25M), inerted, and 2,6-lutidine (1.0 eq.) added. The mixture was heated to an internal temperature of 110° C. for 20 hours. The resulting brown solution was cooled to 20° C. and THF and 25 wt % LiCl aqueous solution added. The phases were separated, and the organic washed three further times with 25 wt % LiCl aqueous solution. 2.0N NaOH (10 eq.) was added to the above organic solution and the mixture was heated to 35° C. for 20 hours before cooling to 20° C. and the phases separated. The organic layer was washed with a mixture of 2.0N HCl acid and brine and the layers separated, the organic layer was washed further with brine and concentrated to give (D2) which was not purified further.

Step 3: tert-butyl(3S)-3-{4-[7-(aminocarbonyl)-2H-indazol-2-yl]phenyl}piperidine-1-carboxylate (D3)

(D2) was dissolved in DCM (0.35M) and di tert-butyl carbonate (1.3 eq.) and pyridine (1.0 eq.) added at RT. After 30 minutes ammonium bicarbonate (1.3 eq.) was added and stirring continued for 20 hours. 1N HCl (5 mL/g) was added and the phases separated, the organic layer was washed twice with water and concentrated to a low volume. The crude compound (D3) was filtered through a pad of silica and then crystallised from methyl tert-butyl ether.

Step 4: (3S)-3-{4-[7-(Aminocarbonyl)-2H-indazol-2-yl]phenyl}piperidinium 4-methylbenzenesulfonate (D4)

(D3) was dissolved in THF (0.15M) and water added (5% compared to THF). para-Toluene sulphonic acid monohydrate (2.2 eq.) was added and the mixture heated to 66° C. and stirred overnight. After cooling the desired solid salt was isolated by filtration and confirmed to be a monohydrate (D4). $^1$H NMR (400 MHz, DMSO, 300K) δ 9.34 (1H, s); 9.20 (1H, broad s), 8.58 (1H, s), 8.14 (2H, d, J=8.8 Hz), 8.05 (2H, ddd, J=1.2, 7.2, 16.8 Hz), 7.93 (1H, s), 7.52 (4H, dd, J=8.8, 16.8 Hz), 7.27 (1H, dd, J=6.8, 8.0 Hz), 7.13 (2H, d, J=8 Hz), 3.48 (3H, m), 3.10 (2H, m), 2.90 (1H, m); 2.30 (3H, s), 1.89 (2H, m), 1.75 (2H, m).

Example 2

(3S)-3-{4-[7-(Aminocarbonyl)-2H-indazol-2-yl]phenyl}piperidinium 4-methylbenzenesulfonate 50 mg of tert-butyl(3S)-3-{4-[7-(aminocarbonyl)-2H-indazol-2-yl]phenyl}piperidine-1-carboxylate (Example 1, D3) as a compound stock solution was reacted with 1 mole equivalent of p-toluenesulfonic acid, added as a 1.0 Molar solution in ethanol. Excess solvent was removed under centrifugal evaporation and 1 mL of ethanol added at ambient room temperature (~25° C.). The resultant solution stirred at 40° C. for 24 hours where a colorless solid precipitated out of solution and was collected via filtration. This solid was analyzed using x-ray powder diffraction, proton NMR, DSC and TGA to confirm the formation of the title salt.

Example 3

((3S)-3-{4-[7-(Aminocarbonyl)-2H-indazol-2-yl]phenyl}piperidinium benzenesulfate 50 mg of tert-butyl(3S)-3-{4-[7-(aminocarbonyl)-2H-indazol-2-yl]phenyl}piperidine-1-carboxylate (Example 1, D3) as a compound stock solution was reacted with 1 mole equivalent of benzenesulfonic acid, added as a 1.0 Molar solution in THF. Excess solvent was removed under centrifugal evaporation and 1 mL of THF added at ambient room temperature (~25° C.). The resultant solution stirred at 40° C. for 24 hours where a colorless solid precipitated out of solution and was collected via filtration. This solid was analyzed using x-ray powder diffraction, proton NMR, DSC and TGA to confirm the formation of the title salt.

Example 4

(3S)-3-{4-[7-(Aminocarbonyl)-2H-indazol-2-yl]phenyl}piperidinium fumarate 50 mg of tert-butyl(3S)-3-{4-[7-(aminocarbonyl)-2H-indazol-2-yl]phenyl}piperidine-1-carboxylate (Example 1, D3) as a compound stock solution was reacted with 1 mole equivalent of fumaric acid, added as a 0.405 Molar solution in ethanol. Excess solvent was removed under centrifugal evaporation and 1 mL of ethanol added at ambient room temperature (~25° C.). The resultant solution stirred at 40° C. for 24 hours. The experiment was left to gently evaporate under atmospheric conditions where a colorless solid was observed. This solid was analyzed using x-ray powder diffraction, proton NMR, DSC and TGA to confirm the formation of the title salt.

Example 5

(3S)-3-{4-[7-(Aminocarbonyl)-2H-indazol-2-yl]phenyl}piperidinium sulfate 50 mg of tert-butyl(3S)-3-{4-[7-(aminocarbonyl)-2H-indazol-2-yl]phenyl}piperidine-1-carboxylate (Example 1, D3) as a compound stock solution was reacted with 1 mole equivalent of sulfuric acid, added as a 1 Molar solution in 1:1 (v/v) methanol:water solution. Excess solvent was removed under centrifugal evaporation and 1 mL of the methanol:water solution added at ambient room temperature (~25° C.). The resultant solution stirred at 40° C. for 24 hours. The experiment was left to gently evaporate under atmospheric conditions where a colorless solid was observed.

The following table compares the physicochemical properties of Example 1 with the corresponding chloride salt.

TABLE 1

Comparison of the physicochemical properties

| Salt form | Hygroscopicity (at 25° C.) | Aqueous solubility (mg/mL) |
|---|---|---|
| Example 1 | Non-hygroscopic (0.3% moisture adsorbed to 95% RH) | 0.8 |
| Chloride salt | Highly hygroscopic (10% moisture to 50% RH and 60% moisture to 95% RH) | >20 |

Chloride salt = (3S)-3-[4-[7-(Aminocarbonyl)-2H-indazol-2-yl]phenyl]piperidinium chloride

What is claimed is:
1. A compound which is:
(3S)-3-{4-[7-(Aminocarbonyl)-2H-indazol-2-yl]phenyl}piperidinium 4-methylbenzenesulfonate monohydrate;
or a stereoisomer or tautomer thereof.

* * * * *

UNITED STATES PATENT AND TRADEMARK OFFICE
CERTIFICATE OF CORRECTION

| | | |
|---|---|---|
| PATENT NO. | : 8,436,185 B2 | Page 1 of 1 |
| APPLICATION NO. | : 12/811922 | |
| DATED | : May 7, 2013 | |
| INVENTOR(S) | : Jennifer R. Foley and Robert Darrin Wilson | |

It is certified that error appears in the above-identified patent and that said Letters Patent is hereby corrected as shown below:

On the title page item (73) should read:

(73) Assignee:  Merck Sharp & Dohme Limited
Hertford Road
Hoddesdon, Hertfordshire, United Kingdom EN11 9BU Signed and Sealed this
Twelfth Day of July, 2016

Michelle K. Lee
*Director of the United States Patent and Trademark Office*